(12) United States Patent
Bakeman et al.

(10) Patent No.: US 9,778,213 B2
(45) Date of Patent: Oct. 3, 2017

(54) METROLOGY TOOL WITH COMBINED XRF AND SAXS CAPABILITIES

(71) Applicant: KLA-Tencor Corporation, Milpitas, CA (US)

(72) Inventors: Michael S. Bakeman, San Jose, CA (US); Andrei V. Shchegrov, Campbell, CA (US); Kevin Peterlinz, Fremont, CA (US); Thaddeus Gerard Dziura, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 581 days.

(21) Appl. No.: 14/461,416

(22) Filed: Aug. 17, 2014

(65) Prior Publication Data

US 2015/0051877 A1 Feb. 19, 2015

Related U.S. Application Data

(60) Provisional application No. 61/867,404, filed on Aug. 19, 2013.

(51) Int. Cl.
```
G06F 17/50    (2006.01)
G01N 23/223   (2006.01)
G01N 23/201   (2006.01)
```
(52) U.S. Cl.
CPC ......... *G01N 23/223* (2013.01); *G01N 23/201* (2013.01); *G01N 2223/6116* (2013.01)

(58) Field of Classification Search
None
See application file for complete search history.

(56) References Cited

U.S. PATENT DOCUMENTS

| | | | |
|---|---|---|---|
| 5,608,526 | A | 3/1997 | Piwonka-Corle et al. |
| 5,859,424 | A | 1/1999 | Norton et al. |

(Continued)

FOREIGN PATENT DOCUMENTS

| | | |
|---|---|---|
| EP | 2589956 A1 | 8/2013 |
| KR | 1020130019030 | 2/2013 |

OTHER PUBLICATIONS

International Search Report and Written Opinion mailed on Dec. 29, 2014, for PCT Application No. PCT/US2014/051741 filed on Aug. 19, 2014, by KLA-Tencor Corporation, 9 pages.

*Primary Examiner* — Craig Dorais
(74) *Attorney, Agent, or Firm* — Spano Law Group; Joseph S. Spano

(57) ABSTRACT

Methods and systems for performing simultaneous X-ray Fluorescence (XRF) and small angle x-ray scattering (SAXS) measurements over a desired inspection area of a specimen are presented. SAXS measurements combined with XRF measurements enables a high throughput metrology tool with increased measurement capabilities. The high energy nature of x-ray radiation penetrates optically opaque thin films, buried structures, high aspect ratio structures, and devices including many thin film layers. SAXS measurements of a particular location of a planar specimen are performed at a number of different out of plane orientations. This increases measurement sensitivity, reduces correlations among parameters, and improves measurement accuracy. In addition, specimen parameter values are resolved with greater accuracy by fitting data sets derived from both SAXS and XRF measurements based on models that share at least one material parameter. The fitting can be performed sequentially or in parallel.

20 Claims, 6 Drawing Sheets

(56) References Cited

U.S. PATENT DOCUMENTS

| | | | |
|---|---|---|---|
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 11/2004 | Janik et al. | |
| 6,895,075 B2 | 5/2005 | Yokhin et al. | |
| 6,972,852 B2 | 12/2005 | Opsal et al. | |
| 7,478,019 B2 | 1/2009 | Zangooie et al. | |
| 7,826,071 B2 | 11/2010 | Shchegrov et al. | |
| 7,929,667 B1 * | 4/2011 | Zhuang | H05G 2/003 378/119 |
| 7,933,026 B2 | 4/2011 | Opsal et al. | |
| 2008/0273662 A1 * | 11/2008 | Yun | G03F 7/70625 378/74 |
| 2009/0067573 A1 * | 3/2009 | Yokhin | G01N 23/2206 378/46 |
| 2012/0051518 A1 * | 3/2012 | Omote | G21K 1/06 378/86 |
| 2013/0304424 A1 | 11/2013 | Bakeman et al. | |
| 2014/0019097 A1 | 1/2014 | Bakeman et al. | |
| 2014/0067316 A1 * | 3/2014 | Ishibashi | G01N 23/201 702/150 |
| 2014/0172394 A1 | 6/2014 | Kuznetsov et al. | |
| 2014/0222380 A1 | 8/2014 | Kuznetsov et al. | |
| 2015/0204664 A1 | 7/2015 | Bringoltz | |
| 2015/0233804 A1 * | 8/2015 | Meisberger | G01N 23/201 378/53 |

\* cited by examiner

METROLOGY TOOL WITH COMBINED XRF AND SAXS CAPABILITIES

CROSS REFERENCE TO RELATED APPLICATION

The present application for patent claims priority under 35 U.S.C. §119 from U.S. provisional patent application Ser. No. 61/867,404, entitled "Metrology Apparatus with SAXS and XRF Capabilities," filed Aug. 19, 2013, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of XRF metrology based techniques including scatterometry and reflectometry implementations and associated analysis algorithms are commonly used to characterize critical dimensions, film thicknesses, composition and other parameters of nanoscale structures.

Traditionally, scatterometry measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for XRF radiation to penetrate to the bottom layers. In addition, the increasing number of parameters required to characterize complex structures (e.g., FinFETs), leads to increasing parameter correlation. As a result, the parameters characterizing the target often cannot be reliably decoupled with available measurements. In another example, opaque, high-k materials are increasingly employed in modern semiconductor structures. XRF radiation is often unable to penetrate layers constructed of these materials. As a result, measurements with thin-film scatterometry tools such as ellipsometers or reflectometers are becoming increasingly challenging.

In response to these challenges, more complex XRF tools have been developed. For example, tools with multiple angles of illumination, shorter and broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

In one example, grazing incidence small angle x-ray scattering (GISAXS) is combined with x-ray reflectometry (XRR) for surface layer characterization of thin films as presented in U.S. Pat. No. 6,895,075, entitled "X-Ray Reflectometry With Small-Angle Scattering Measurement," issued on May 17, 2005, and assigned to Jordan Valley Applied Radiation Ltd. These techniques are sensitive to surfaces, but not to buried structures or films below the surface. In addition, the spot sizes of the probe beams are greatly increased due to the shallow incidence angles employed in these techniques. Although large spot sizes can be mitigated using, for example, apertures or knife edges, this results in an undesirable reduction in flux and increase in measurement time.

Future metrology applications present challenges for metrology due to increasingly small resolution requirements, multi-parameter correlation, increasingly complex geometric structures, and increasing use of opaque materials. Thus, methods and systems for improved CD measurements are desired.

SUMMARY

Methods and systems for performing critical dimension measurements are presented. Such systems are employed to measure structural and material characteristics (e.g., material composition, dimensional characteristics of structures and films, etc.) associated with different semiconductor fabrication processes.

In one aspect, a single metrology tool performs simultaneous x-ray fluorescence (XRF) and small angle x-ray scattering (SAXS) measurements over an inspection area of a specimen. SAXS measurements combined with XRF measurements enables a metrology tool with increased measurement capabilities due to the complementary nature of SAXS and XRF techniques. SAXS is capable of measuring geometric parameters (e.g., pitch, critical dimension (CD), side wall angle (SWA), line width roughness (LWR), and line edge roughness (LER)) of structures smaller than 10 nanometers. In addition, the high energy nature of x-ray radiation penetrates optically opaque thin films, buried structures, high aspect ratio structures, and devices including many thin film layers. XRF techniques are capable of measuring thin film thickness and composition of many different structures.

In another aspect, the precision and accuracy of parameters measured with combined SAXS and XRF techniques is improved by identifying shared model parameters that can be mathematically resolved using data sets derived from SAXS and XRF measurements either sequentially or in parallel. Measuring shared parameters with a diversity of measurement technologies reduces correlations among parameters and improves measurement accuracy.

In yet another aspect, SAXS measurements performed on a planar specimen (e.g., semiconductor wafer) oriented at a number of different out of plane orientations increases the precision and accuracy of measured parameters. Measuring a location of the specimen at a number of different angles results in an enhanced data set corresponding to that location. Measuring parameters with a deeper, more diverse data set also reduces correlations among parameters and improves measurement accuracy.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
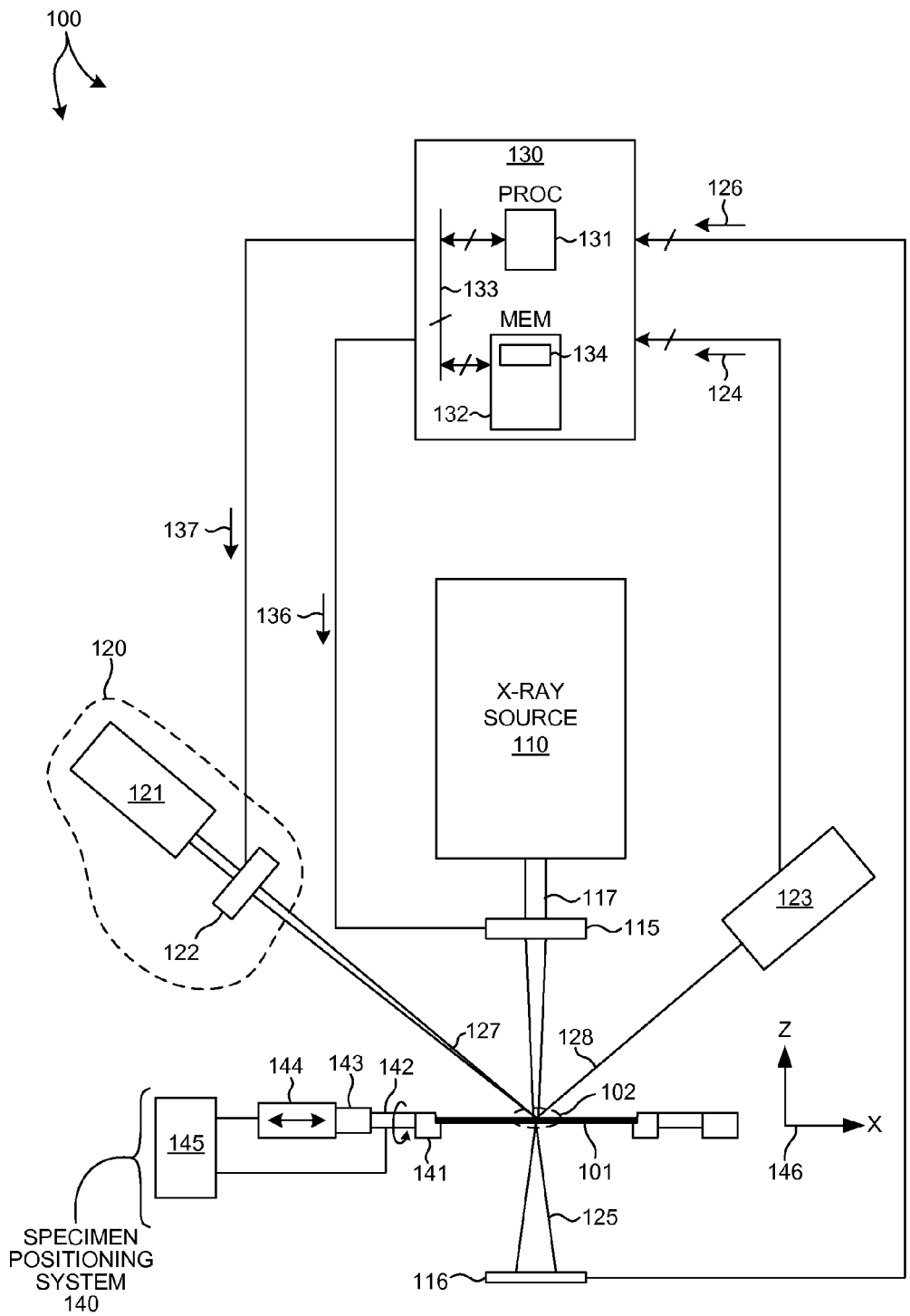
FIG. 1 is a diagram illustrative of a combined metrology system 100 configured to combine small angle x-ray scatterometry (SAXS) and x-ray fluorescence (XRF) metrologies in accordance with the methods described herein.

Reference will now be made in detail to background examples and some embodiments of the invention, examples of which are illustrated in the accompanying drawings. Methods and systems for performing measurements of semiconductor structures and materials with a combination of Small-Angle X-Ray Scattering (SAXS) and X-Ray Fluorescence (XRF) measurement modalities are presented. Such systems are employed to measure structural and material characteristics (e.g., material composition, dimensional characteristics of structures and films, etc.) associated with different semiconductor fabrication processes.

The combined use of XRF and high brightness SAXS (in either grazing incidence or transmission incidence configurations) enables high flux x-ray radiation penetration into opaque areas of the target. Examples of measureable geometric parameters using combined SAXS and XRF include pore size, pore density, line edge roughness, line width roughness, side wall angle, profile, film thickness, critical dimension, pitch. Examples of measureable material parameters include electron density, elemental identification and composition. In some examples, combined SAXS and XRF enable the measurement of features smaller than 10 nm as well as advanced semiconductor structures such as spin-transfer-torque MRAM where measurements of geometrical parameters and material parameters are needed.

In one aspect, a combined metrology tool performs simultaneous XRF and SAXS measurements over an inspection area of a specimen. A metrology tool combining SAXS measurements and XRF measurements enables increased measurement sensitivity and throughput due to the complementary nature of SAXS and XRF techniques. By way of non-limiting example, SAXS is capable of measuring geometric parameters (e.g., pitch, critical dimension (CD), side wall angle (SWA), line width roughness (LWR), and line edge roughness (LER)) of structures smaller than 10 nanometers. By way of non-limiting example, XRF techniques are capable of measuring thin film thickness, and composition of many different structures. The high energy nature of x-ray radiation penetrates optically opaque thin films, buried structures, high aspect ratio structures, and devices including many thin film layers.

SAXS and XRF applied in combination as described herein may be used to determine characteristics of a variety of semiconductor structures. Exemplary structures include, but are not limited to, FinFETs, low-dimensional structures such as nanowires or graphene, sub 10 nm structures, thin films, lithographic structures, through silicon vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, film thickness, critical dimension, pitch, and material parameters such as electron density, composition, and elemental identification.

FIG. 1 illustrates an embodiment of a combined metrology tool 100 for measuring characteristics of a specimen in accordance with the exemplary methods presented herein. As shown in FIG. 1, the system 100 may be used to perform XRF measurements and transmission SAXS measurements over an inspection area 102 of a specimen 101 disposed on a specimen positioning system 140. In some embodiments, the inspection area 102 has a spot size of fifty micrometers or less.

In the depicted embodiment, metrology tool 100 includes an x-ray illumination source 110 configured to generate x-ray radiation suitable for SAXS measurements. In some embodiments, the x-ray illumination system 110 is configured to generate wavelengths between 0.01 nanometers and 1 nanometer. X-ray illumination source 110 produces an x-ray beam 117 incident on inspection area 102 of specimen 101.

X-ray optics 115 shape and direct incident x-ray beam 117 to specimen 101. In some examples, x-ray optics 115 monochromatize the x-ray beam that is incident on the specimen 101. In some examples, x-ray optics 115 collimate or focus the x-ray beam 117 onto inspection area 102 of specimen 101 to less than 1 milliradian divergence using multilayer x-ray optics. In some embodiments, x-ray optics 115 includes one or more x-ray collimating mirrors, x-ray apertures, x-ray monochromators, and x-ray beam stops, or any combination thereof.

X-ray detector 116 collects x-ray radiation 125 scattered from specimen 101 and generates an output signal 126 indicative of properties of specimen 101 that are sensitive to the incident x-ray radiation in accordance with a SAXS measurement modality. Scattered x-rays 125 are collected by x-ray detector 116 while specimen positioning system 140 locates and orients specimen 101 to produce angularly resolved scattered x-rays. The x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, and a scintillator.

By way of non-limiting example, the small angle x-ray scatterometer illustrated in FIG. 1 is configured as a transmission small angle x-ray scatterometer. However, in some other embodiments combined metrology tool 100 includes a grazing incidence small angle x-ray scatterometer.

Combined metrology tool 100 also includes an x-ray illumination source 120 configured to generate x-ray radiation suitable for XRF measurements. In some embodiments, the x-ray illumination system 120 is configured to generate wavelengths between 0.01 nanometers and 1 nanometer. X-ray illumination source 120 produces an x-ray beam 127 incident on inspection area 102 of specimen 101.

X-ray optics 122 shape and direct incident x-ray beam 127 to specimen 101. In some examples, x-ray optics 122 monochromatize the x-ray beam that is incident on the specimen 101. In some examples, x-ray optics 122 collimate or focus the x-ray beam 127 onto inspection area 102 of specimen 101. In some embodiments, x-ray optics 122 includes one or more x-ray collimating mirrors, x-ray apertures, x-ray monochromators, and x-ray beam stops, or any combination thereof.

X-rays 128 are collected by x-ray detector 123 while specimen positioning system 140 locates and orients specimen 101. The x-ray detector 123 is able to resolve one or more x-ray photon energies and produces signals for each x-ray energy component indicative of properties of the specimen. In some embodiments, the x-ray detector 123 includes any of a CCD array, a microchannel plate, a photodiode array, a microstrip proportional counter, a gas filled proportional counter, and a scintillator.

X-ray detector 123 collects x-ray radiation 128 fluoresced from specimen 101 and generates an output signal 124 indicative of properties of specimen 101 that are sensitive to the incident x-ray radiation in accordance with a XRF measurement modality. By way of non-limiting example, the XRF measurement system illustrated in FIG. 1 includes an energy dispersive XRF detector suitable for performing measurements in accordance with an energy dispersive XRF measurement modality. However, in some other embodiments the XRF measurement system includes a wavelength dispersive XRF detector suitable for performing measurements in accordance with a wavelength dispersive XRF measurement modality.

In yet another example, the XRF measurement system illustrated in FIG. 1 is configured as a Total Reflection XRF (TXRF) measurement system. In these embodiments, the incident angle of the XRF illumination beam is below the critical angle for the substrate. In some examples an angle of incidence of approximately 0.05 degrees is employed. TXRF limits the excitation of the sample to the outermost surface and can be used to measure surface metal contamination on wafers, or conformal layers, such as a conformal layer of Germanium over a FinFET structure. TXRF can be used to perform on-device measurements, and is not limited to the small spot (e.g., approximately 50 micrometers, or less) typically required for metrology targets. Due to the larger permissible spot size, a larger incident x-ray flux may be directed to the surface of the specimen under measurement. The resulting reduction in measurement time is desireable, particularly when a wavelength dispersive detector is employed.

In yet another example, the XRF measurement system illustrated in FIG. 1 is configured as a confocal XRF measurement system. In these embodiments, illumination optics such as illumination optics 122 are configured to collimate the incident x-ray radiation over a small volume of the specimen 101 under inspection. Similarly, collection optics (not shown) are employed to collect fluoresced radiation from the illuminated volume and project the collected radiation onto detector 123. In some embodiments, the illumination and collection optics are polycapillary optics. In confocal XRF, the field of view of the illumination and collection optics is relatively small (e.g., less than 100 um$^3$, or approximately 10 um$^3$ in some cases) compared to conventional XRF measurements. In this manner, spatially resolved, localized thin film and composition measurements can be performed using confocal XRF with a high degree of precision.

In some embodiments, the x-ray detectors 116 and 123 are maintained in the same atmospheric environment as specimen 101 (e.g., gas purge environment). However, in some embodiments, the distance between specimen 101 and x-ray detector 116 or x-ray detector 123 is lengthy (e.g., greater than one meter). In these embodiments, environmental disturbances (e.g., air turbulence) contribute noise to the detected signals. Hence in some embodiments, one or more of the x-ray detectors is maintained in a localized, vacuum environment separated from the specimen (e.g., specimen 101) by a vacuum window.

Figure 4:
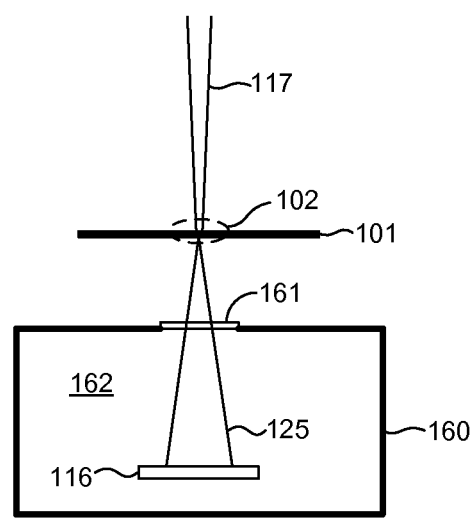
FIG. 4 is a diagram illustrative of a x-ray detector 116 of combined metrology systems 100 and 400 contained in a vacuum environment 162 separate from specimen 101.

FIG. 4 is a diagram illustrative of a vacuum chamber 160 containing x-ray detector 116 in one embodiment. In a preferred embodiment, vacuum chamber 160 includes a substantial portion of the path between specimen 101 and x-ray detector 116. An opening of vacuum chamber 160 is covered by vacuum window 161. Vacuum window 161 may be constructed of any suitable material that is substantially transparent to x-ray radiation (e.g., Beryllium). Scattered x-ray radiation 125 passes through vacuum window 161, enters vacuum chamber 160 and is incident on x-ray detector 116. A suitable vacuum environment 162 is maintained within vacuum chamber 160 to minimize disturbances to scattered x-ray radiation 125. X-ray detector 123 may also be maintained in a localized, vacuum environment separated from the specimen in a similar manner.

Combined metrology tool 100 also includes a computing system 130 employed to acquire signals 124 and 126 generated by XRF detector 123 and SAXS detector 116, respectively, and determine properties of the specimen based at least in part on the acquired signals. As illustrated in FIG. 1, computing system 130 is communicatively coupled to XRF detector 123 and SAXS detector 116.

In some embodiments, the incident XRF illumination beam 127 and the incident SAXS illumination beam 117 spatially overlap at the inspection area 102 of the specimen 101. Furthermore, in some embodiments, the incident XRF illumination beam 127 and the incident SAXS illumination beam 117 spatially overlap at the inspection area 102 of the specimen 101 at the same time. Thus, in one aspect, computing system 130 receives measurement data 124 and 126 associated with simultaneous, critical dimension measurements of specimen 101 over an inspection area 102 illuminated by both an x-ray beam 117 configured for SAXS measurements and an x-ray beam 127 configured for XRF measurements.

In one example, XRF detector 123 is a wavelength dispersive XRF spectrometer and measurement data 124 includes an indication of the measured spectral response of the specimen based on one or more sampling processes implemented by the XRF spectrometer.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In general, any suitable high-brightness x-ray illumination source capable of generating high brightness x-rays at flux levels sufficient to enable high-throughput, inline metrology may be contemplated to supply x-ray illumination for either, or both, SAXS and XRF measurements. In some embodiments, one or more x-ray sources emitting radiation with a brightness greater than 15 keV are employed.

Exemplary x-ray sources include electron beam sources configured to bombard solid or liquid targets to stimulate x-ray radiation. Methods and systems for generating high brightness, liquid metal x-ray illumination are described in U.S. Pat. No. 7,929,667, issued on Apr. 19, 2011, to KLA-Tencor Corp., the entirety of which is incorporated herein by reference. In another example, an inverse Compton source available from Lyncean Technologies, Inc., Palo Alto, Calif. (USA) may be contemplated.

In yet another aspect, secondary x-ray targets can be placed in front of the XRF x-ray source, causing the secondary targets to fluoresce. The secondary fluorescence can then be used to excite the specimen to be measured. This is useful for two purposes. First, an x-ray source employing an electron beam such as a rotating anode or a liquid metal jet illumination source will generate background radiation called bremsstrahlung. Bremsstrahlung radiation arises from the interaction of the electron beam with the primary target. This background radiation shows up as noise in measurements of samples illuminated, in part, by this radiation. To minimize bremsstrahlung radiation, a secondary target is introduced into the illumination system. The primary radiation generated by the interaction of the electron beam with the primary target is used to excite the secondary target. The emission from the secondary target does not include bremsstrahlung radiation because the secondary target is excited by photons rather than electrons. The emission from the secondary target is then used to illuminate the sample, rather than the emission from the primary target. This increases the signal to noise of an XRF measurement. Secondly, since the radiation from a secondary target is emitted at the characteristic energy levels of the secondary target, a change in material composition of the secondary target can be used to change the x-ray energy incident upon the sample. This is useful to increase the x-ray absorption of elements whose absorption edges are far from the primary target energies. Again, this is useful for increasing the signal to noise of an XRF measurement. Thus, in some embodiments, the XRF illumination source (e.g., illumination source 120) includes multiple interchangeable secondary target materials to deliver tunable radiation to the specimen under measurement.

In one further aspect, combined metrology tool 100 includes a computing system (e.g., computing system 130) configured to implement beam control functionality as described herein. In the embodiment depicted in FIG. 1, computing system 130 is configured as a beam controller operable to control the positioning and spot size of the incident SAXS illumination beam 117 and the incident XRF illumination beam 127 such that they spatially overlap at the desired inspection area 102 of the specimen 101 at any point in time.

As illustrated in FIG. 1, computing system 130 is communicatively coupled to SAXS detector 116 and XRF detector 123. Computing system 130 is configured to receive measurement data 124 from XRF detector 123 and measurement data 126 from SAXS detector 116. In one example, measurement data 124 includes an indication of the measured XRF response of the specimen. Based on the distribution of the measured XRF response on the surface of detector 123, the location and area of incidence of XRF illumination beam 127 on specimen 101 is determined by beam controller 130. In one example, pattern recognition techniques are applied by computing system 130 to determine the location and area of incidence of XRF illumination beam 127 on specimen 101 based on measurement data 124. Similarly, measurement data 126 includes an indication of the measured SAXS response of the specimen. Based on the distribution of the measured SAXS response on the surface of detector 116, the location and area of incidence of SAXS illumination beam 117 on specimen 101 is determined by beam controller 130. In one example, pattern recognition techniques are applied by computing system 130 to determine the location and area of incidence of SAXS illumination beam 117 on specimen 101 based on measurement data 126. In response computing system 130 generates a command signal 137 communicated to illumination optics 122 to redirect and reshape incident XRF illumination beam 127 such that incident XRF illumination beam 127 spatially overlaps incident x-ray beam 117 at the desired inspection area 102 of specimen 101. Similarly, beam controller 130 generates a command signal 136 communicated to x-ray optics 115 to redirect and reshape SAXS illumination beam 117 such that incident SAXS illumination beam 117 spatially overlaps incident XRF illumination beam 127 at the desired inspection area 102 of specimen 101.

In another aspect, simultaneous SAXS and XRF measurements of a particular inspection area are performed at a number of different out of plane orientations. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy.

As illustrated in FIG. 1, combined metrology tool 100 includes a specimen positioning system 140 configured to both align specimen 101 and orient specimen 101 over a large range of out of plane angular orientations with respect to the XRF and the SAXS scatterometer. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 1, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 1, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

For example, in a normal orientation, SAXS is able to resolve the critical dimension of a feature, but is largely insensitive to sidewall angle and height of a feature. However, by collecting measurement data over a broad range of out of plane angular positions, the sidewall angle and height of a feature can be resolved.

In yet another aspect, the precision and accuracy of parameters measured with combined SAXS and XRF techniques can be improved by identifying shared model parameters that are mathematically resolved using data sets derived from SAXS and XRF measurements either sequentially or in parallel. Measuring shared parameters with a diversity of measurement technologies reduces correlations among parameters and improves measurement accuracy.

In general, the SAXS and XRF techniques discussed herein are indirect methods of measuring some physical properties of the specimen under inspection. In most cases, the measured values cannot be used to directly determine the physical properties of the specimen. The nominal measurement process consists of parameterization of the structure (e.g., film thicknesses, critical dimensions, etc.) and the machine (e.g., wavelengths, angles of incidence, polarization angles, etc.). A model is created that attempts to predict the measured values. The model includes parameters associated with the machine ($P_{machine}$) and the specimen ($P_{specimen}$).

Machine parameters are parameters used to characterize the metrology tool itself. Exemplary machine parameters include angle of incidence (AOI), illumination wavelength, numerical aperture (NA), etc. Specimen parameters are parameters used to characterize the specimen. For a thin film specimen, exemplary specimen parameters include refractive index, dielectric function tensor, nominal layer thickness of all layers, layer sequence, etc. For measurement purposes, the machine parameters are treated as known, fixed parameters and the specimen parameters are treated as unknown, floating parameters. The floating parameters are resolved by a fitting process (e.g., regression, library matching, etc.) that produces the best fit between theoretical predictions and experimental data. The unknown specimen parameters, $P_{specimen}$, are varied and the model output values are calculated until a set of specimen parameter values are determined that results in a close match between the model output values and the experimentally measured values.

In another further aspect, combined metrology tool 100 includes a computing system configured to generate a structural model (e.g., geometric model, material model, or combined geometric and material model) of a measured structure of a specimen, generate an XRF response model and a SAXS response model that each include at least one shared geometric parameter from the structural model, and resolve at least one specimen parameter value by performing a fitting analysis of XRF measurement data with the XRF response model and a fitting analysis on SAXS measurement data with the SAXS response model. The analysis engine is used to compare the simulated SAXS and XRF signals with measured data thereby allowing the determination of geometric as well as material properties such as electron density and elemental identification and composition of the sample. In the embodiment depicted in FIG. 1, computing system 130 is configured as a model building and analysis engine configured to implement model building and analysis functionality as described herein.

Figure 3:
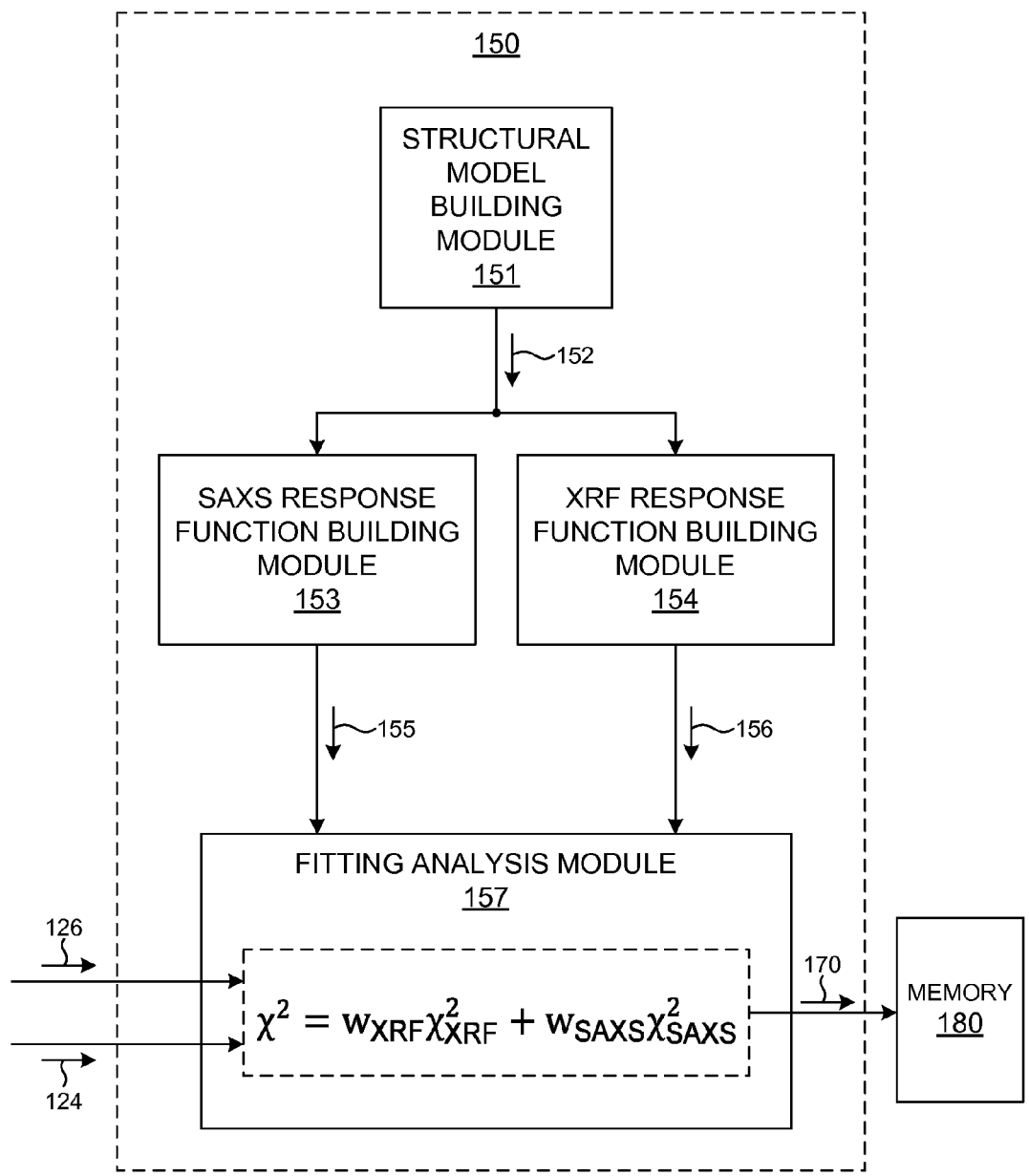
FIG. 3 is a diagram illustrative of a model building and analysis engine 150 configured to resolve specimen parameter values based on SAXS and XRF metrology data in accordance with the methods described herein.

FIG. 3 is a diagram illustrative of an exemplary model building and analysis engine 150 implemented by computing system 130. As depicted in FIG. 3, model building and analysis engine 150 includes a structural model building module 151 that generates a structural model 152 of a measured structure of a specimen. In some embodiments, structural model 152 also includes material properties of the specimen. The structural model 152 is received as input to SAXS response function building module 153 and XRF response function building module 154. SAXS response function building module 153 generates a SAXS response function model 155 based at least in part on the structural model 152. In some examples, the SAXS response function model 155 is based on x-ray form factors $$F(\vec{q}) = \int \rho(\vec{r}) e^{-i\vec{q}\cdot\vec{r}} d\vec{r} \quad (1)$$

where F is the form factor, q is the scattering vector, and ρ(r) is the electron density of the specimen in spherical coordinates. The x-ray scattering intensity is then given by $$I(\vec{q}) = F^*F \quad (2)$$

Similarly, XRF response function building module 154 generates a XRF response function model 156 based at least in part on the structural model 152. In some examples, the XRF response function model 156 is based on the intensity of fluoresced radiation for a specific element given by equation (3).

$$I_X(s_n) = I_\gamma \frac{\tau \rho \omega R}{\left(\frac{\mu_\gamma(s_n)}{\cos\phi} + \frac{\mu_x(s_n)}{\cos\theta}\right)} \left\{1 - \exp\left[-\left(\frac{\mu_\gamma(s_n)}{\cos\phi} + \frac{\mu_x(s_n)}{\cos\theta}\right)L\right]\right\} \frac{\Omega}{4\pi\cos\theta} \quad (3)$$

where, $I_X$ is the x-ray rate at the detector surface at fluoresced energy x for element s; $I_\gamma$ is the x-ray rate at the sample surface at excitation energy, γ; τ is the photoelectric cross section of excitation energy, γ; ρ is the concentration (i.e., density) of element, s; ω is the K(L) fluorescence yield; R is the radiative rate for K(L); $\mu_\gamma$ is the linear attenuation coefficient at energy, γ, for a slab with element $s_n$; $\mu_X$ is the linear attenuation coefficient at energy, X, for a slab with element $s_n$; φ is the incident angle of the x-ray; and θ is the exiting angle of the x-ray; and L is the slab (i.e., layer) thickness.

SAXS response function model 155 and XRF response function model 156 are received as input to fitting analysis module 157. The fitting analysis module 157 compares the modeled SAXS and XRF with the corresponding measured data to determine geometric as well as material properties of the specimen.

In some examples, the fitting of modeled data to experimental data is achieved by minimizing a chi-squared value. For example, for XRF metrology, a chi-squared value can be defined as $$\chi^2_{XRF} = \frac{1}{N_{XRF}} \sum_i^{N_{XRF}} \frac{\left(S_i^{XRF \cdot model}(u_1, \ldots, u_M) - S_i^{XRF \cdot experiment}\right)^2}{\sigma^2_{XRF,i}} \quad (4)$$

where $S_i^{XRF \cdot experiment}$ is the measured XRF signals 124 measured experimentally in the "channel" i, where the index i describes a set of system parameters such as energy, angular coordinate, etc. $S_i^{XRF \cdot model}(u_1, \ldots, u_M)$ is the modeled XRF signal for the "channel" i, evaluated for a set of structure (target) parameters $u_1, \ldots, u_M$, where these parameters describe geometric (film thicknesses, CD, sidewall angle, overlay, etc.) and material (refractive indices, absorption coefficients, dispersion model parameters), etc. $\sigma_{XRF,i}$ is the uncertainty associated with "channel" i. $N_{XRF}$ is the total number of channels in the XRF metrology. M is the number of parameters characterizing the metrology target.

Similarly, for SAXS measurements, a chi-squared value can be defined as $$\chi^2_{SAXS} = \frac{1}{N_{SAXS}} \sum_j^{N_{SAXS}} \frac{\left(S_j^{SAXS \; model}(v_1, \ldots, v_L) - S_j^{SAXS \; experiment}\right)^2}{\sigma^2_{SAXS,j}} \quad (5)$$

Where, $S_j^{SAXS \; experiment}$ is the measured SAXS signals 126 in the "channel" j, where the index j describes a set of system parameters such as energy, angular coordinate, etc. $S_j^{SAXS \; model}(v_1, \ldots, v_L)$ is the modeled SAXS signal $S_j$ for the "channel" j, evaluated for a set of structure (target) parameters $v_1, \ldots, v_L$, where these parameters describe geometric (film thicknesses, CD, sidewall angle, overlay, etc.) and material (electron density, etc.). $\sigma_{SAXS,j}$ is the uncertainty associated with the jth channel. $N_{SAXS}$ is the total number of channels in the x-ray metrology. L is the number of parameters characterizing the metrology target.

Equations (4) and (5) assume that the uncertainties associated with different channels are uncorrelated. In examples where the uncertainties associated with the different channels are correlated, a covariance between the uncertainties, can be calculated. In these examples a chi-squared value for XRF measurements can be expressed as $$\chi^2_{XRF} = \frac{1}{N_{XRF}} \left(\vec{S}_i^{XRF \cdot model}(u_1, \ldots, u_M) - \vec{S}_i^{XRF \cdot experiment}\right)^T$$

$$V_{XRF}^{-1}\left(\vec{S}_i^{XRF \cdot model}(u_1, \ldots, u_M) - SiXRF \cdot \text{experiment}\right)$$

where, $V_{XRF}^{(5)}$ is the covariance matrix of the XRF channel uncertainties, and T denotes the transpose. A chi-squared value for SAXS measurements can be calculated in the same manner.

The set of target parameters for the XRF model (i.e., $\{u_1, \ldots, u_M\}$) and the SAXS model (i.e., $\{v_1, \ldots, v_L\}$) are not the same in general. The reason is that the difference in material constants and functions needed to describe XRF and SAXS interaction processes give rise to different target parameters. However, in some embodiments, at least one geometric or material parameter is common between the SAXS response function model 155 and the XRF response function model 156. The common parameter is either identical or related to each other by an unambiguous algebraic transformation. In some examples, target parameters such as film thicknesses, CD, overlay, etc. are common between both the SAXS response function model 155 and the XRF response function model 156.

In some examples, fitting analysis module 157 resolves at least one specimen parameter value by sequentially performing a fitting analysis on XRF measurement data 124 with the XRF response model 156 and a fitting analysis on SAXS measurement data 126 with the SAXS response model 155. In some examples, $\chi_{XRF}^2$ is optimized first, and any resolved, common specimen parameter values are treated as constants in the subsequent optimization of $\chi_{SAXS}^2$. Similarly, in some other examples, $\chi_{SAXS}^2$ is optimized first, and any resolved, common specimen parameter values are treated as constants in the subsequent optimization of $\chi_{XRF}^2$.

In some other examples, fitting analysis module 157 resolves at least one specimen parameter value by performing a parallel fitting analysis on SAXS measurement data 126 with the SAXS response model 155 and on XRF measurement data 124 with the XRF response model 156. For example, a chi-squared function suitable for parallel analysis can be defined as $$\chi^2 = w_{XRF}\chi_{XRF}^2 + w_{SAXS}\chi_{SAXS}^2 \quad (6)$$

where $w_{XRF}$ and $w_{SAXS}$ are weighting coefficients that are assigned to the XRF and SAXS metrologies, respectively. In the simplest case, $w_{XRF}=w_{SAXS}=1$. However; assigning different weights often enhances the more relevant metrology. The selection of proper weights is usually done by analysis of experimental data versus reference metrology and/or measuring pre-programmed design of experiments (DOE) parameter variations on special DOE targets.

XRF and SAXS metrologies may contain more than one respective technology when calculating chi-squared values. For example, $\chi_{SAXS}^2$ may be calculated for the combined use of grazing incidence SAXS and transmission SAXS with a weight coefficient given to each technology. Likewise, $\chi_{XRF}^2$ may be calculated for the combined use of XRF and TXRF with a weight coefficient assigned to each technology.

As described hereinbefore, the fitting of SAXS and XRF data is achieved the minimization of chi-squared values. However, in general, the fitting of SAXS and XRF data may be achieved by other functions.

The combined fitting of XRF metrology data and SAXS metrology data is advantageous for any type of SAXS and XRF technology that provides complementary sensitivity to geometric and/or material parameters of interest. This is specifically the case where at least one geometric (e.g., film thickness) or material parameter is common between the SAXS and the XRF models. Specimen parameters can be deterministic (e.g., film thicknesses, CD, SWA, etc.) or statistical (e.g., rms height of sidewall roughness, roughness correlation length, etc.) as long as proper models describing SAXS and XRF beam interaction with the specimen are used.

Model building and analysis engine 150 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In some embodiments, such as the embodiment depicted in FIG. 1, the combined measurement system includes one x-ray source for SAXS measurements and another x-ray source for XRF measurements. However, in some other embodiments, the same x-ray source generates x-ray illumination for both SAXS and XRF measurements.

Figure 2:
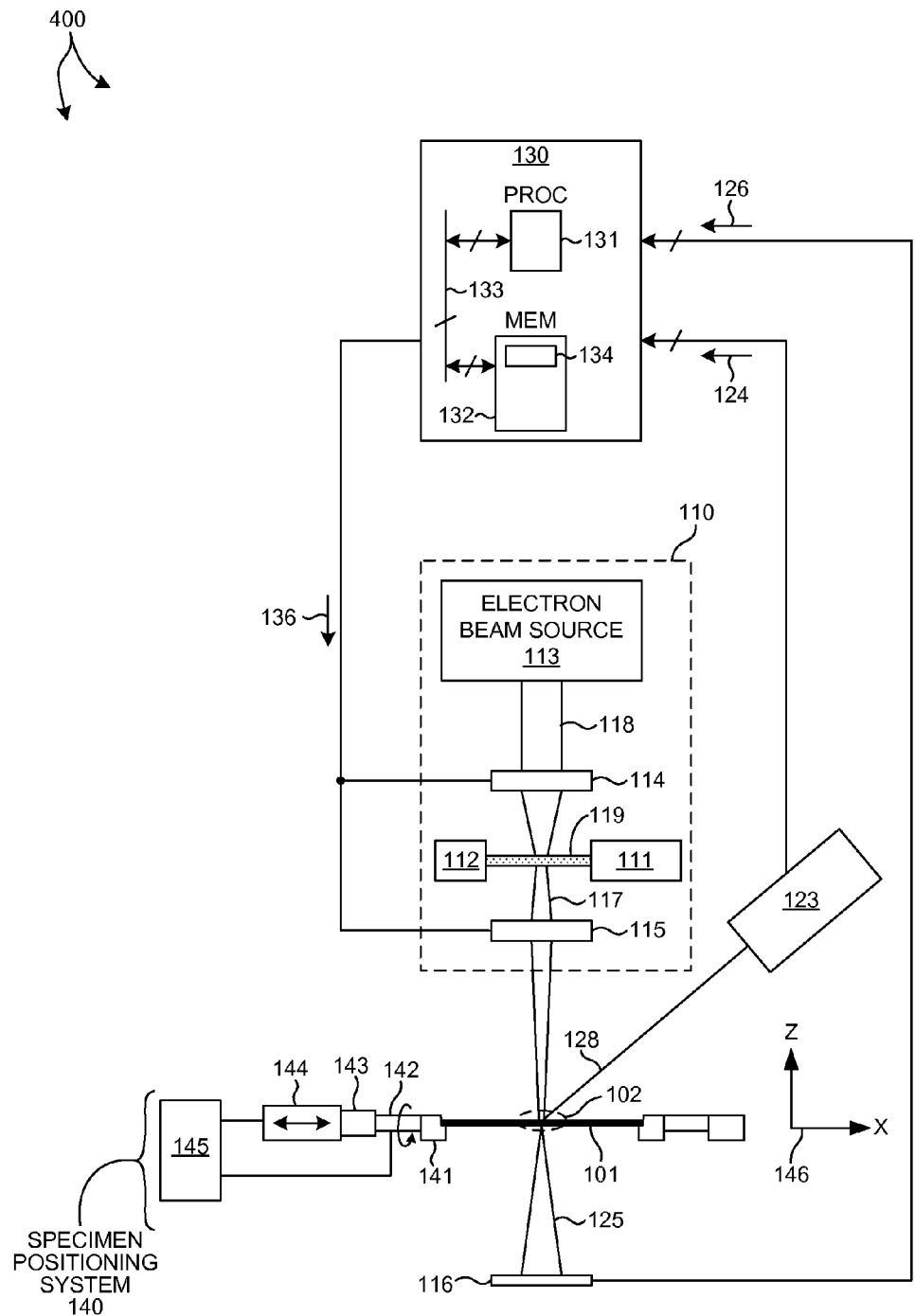
FIG. 2 is a diagram illustrative of a combined metrology system 400 in another embodiment configured to combine SAXS and XRF metrologies in accordance with the methods described herein.

FIG. 2 depicts a combined metrology tool 400 for measuring characteristics of a specimen in accordance with the exemplary methods presented herein. Like numbered elements of combined metrology tool 100 and 400 are analogous. As shown in FIG. 2, the system 400 is used to perform XRF measurements and SAXS measurements over an inspection area 102 of a specimen 101 disposed on a specimen positioning system 140.

In another aspect, combined metrology tool 400 includes an x-ray illumination source 110 that supplies x-ray illumination to specimen 101 for both XRF and SAXS measurements. In some embodiments, both the XRF and SAXS measurements are performed simultaneously based on radiation collected from the specimen in response to illumination provided by x-ray illumination source 110. In the embodiment depicted in FIG. 2, x-ray illumination source 110 is a liquid metal based x-ray illumination system. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. In one embodiment, the jet of liquid metal includes a Gallium and Indium alloy. In some embodiments, the x-ray illumination system 110 is configured to generate wavelengths between 0.01 nanometers and 1 nanometer. Exemplary methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101.

In one embodiment, a combination of transmissive SAXS and energy dispersive XRF metrologies is employed. The incident x-ray beam 117 is at the Indium kα line of 24.2 keV. The x-ray beam is collimated down to less than one milliradian divergence using multi-layer x-ray optics for transmission SAXS measurements. The XRF measurements are collected from radiation stimulated by the same incident x-ray beam and detected by an energy dispersive XRF detector 123. This ensures that the SAXS and XRF response signals are derived from the same measurement target. In addition, in this embodiment, the SAX and XRF signals are collected simultaneously. In some embodiments, the measurement target is an in-die target. In other words, the measurements are performed on an actual device target, rather than a proxy target having larger dimensions.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the XRF detector 123, the SAXS detector 116, the XRF illumination optics 122, and the SAXS illumination optics 115 in any manner known in the art. For example, the one or more computing systems 130 may be coupled to computing systems associated with the XRF detector 123, the SAXS detector 116, the XRF illumination optics 122, and the SAXS illumination optics 115, respectively. In another example, any of the XRF detector 123, the SAXS detector 116, the XRF illumination optics 122, and the SAXS illumination optics 115 may be controlled directly by a single computer system coupled to computer system 130.

The computer system 130 of the combined metrology system 100 may be configured to receive and/or acquire data or information from the subsystems of the system (e.g., XRF detector 123, the SAXS detector 116, the XRF illumination optics 122, and the SAXS illumination optics 115, and the like) by a transmission medium that may include wireline and/or wireless portions. In this manner, the transmission medium may serve as a data link between the computer system 130 and other subsystems of the system 100.

Computer system 130 of the combined metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 124 and 126) from a storage medium (i.e., memory 132 or memory 180) via a data link. For instance, spectral results obtained using a spectrometer of any of SAXS detector 116 and XRF detector 123 may be stored in a permanent or semi-permanent memory device (e.g., memory 132 or 180). In this regard, the spectral results may be imported from on-board memory or from an external memory system. Moreover, the computer system 130 may send data to other systems via a transmission medium. For instance, specimen parameter values 170 determined by computer system 130 may be stored in a permanent or semi-permanent memory device (e.g., memory 180). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a combined SAXS and XRF analysis as described herein is implemented as part of a fabrication process tool. Examples of fabrication process tools include, but are not limited to, lithographic exposure tools, film deposition tools, implant tools, and etch tools. In this manner, the results of a combined SAXS and XRF analysis are used to control a fabrication process. In one example, SAXS and XRF measurement data collected from one or more targets is sent to a fabrication process tool. The SAXS and XRF measurement data is analyzed as described herein and the results used to adjust the operation of the fabrication process tool.

Figure 5:
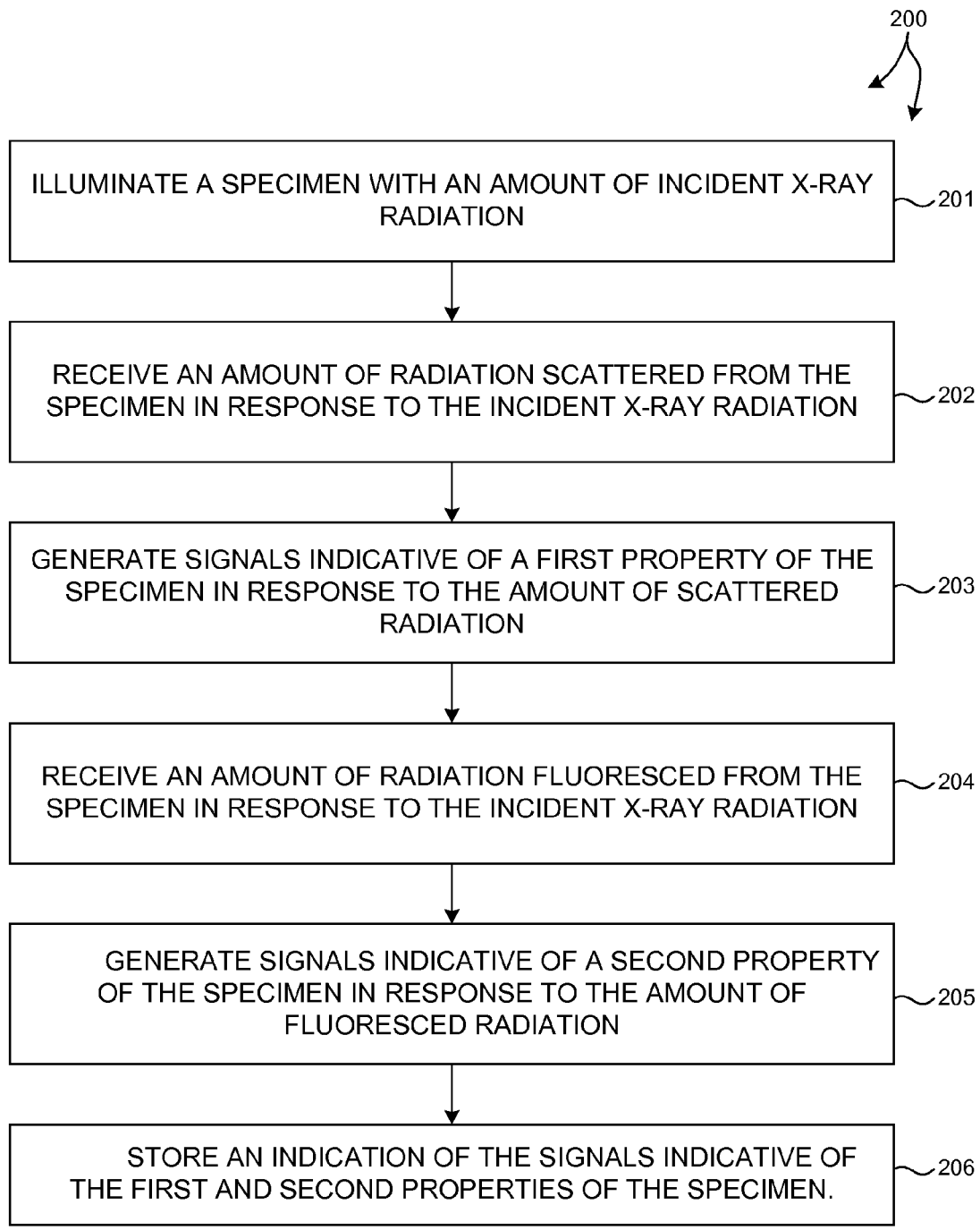
FIG. 5 is a flowchart illustrative of an exemplary method 200 of performing XRF and SAXS measurements over an inspection area of a specimen.

FIG. 5 illustrates a method 200 suitable for implementation by the combined metrology system 100 of the present invention. In one aspect, it is recognized that data processing blocks of method 200 may be carried out via a pre-programmed algorithm executed by one or more processors of computing system 130. While the following description is presented in the context of combined metrology systems 100 and 400, it is recognized herein that the particular structural aspects of combined metrology systems 100 and 400 do not represent limitations and should be interpreted as illustrative only.

In block 201, a specimen is illuminated by an amount of incident x-ray radiation.

In block 202, an amount of radiation scattered from the specimen in response to the incident x-ray radiation is received.

In block 203, signals indicative of a first property of the specimen are generated in response to the amount of scattered radiation.

In block 204, an amount of radiation fluoresced from the specimen in response to the incident x-ray radiation is received.

In block 205, signals indicative of a second property of the specimen are generated in response to the amount of fluoresced radiation.

In block 206, an indication of the signals indicative of the first and second properties of the specimen are stored in a memory (e.g., memory 132).

Figure 6:
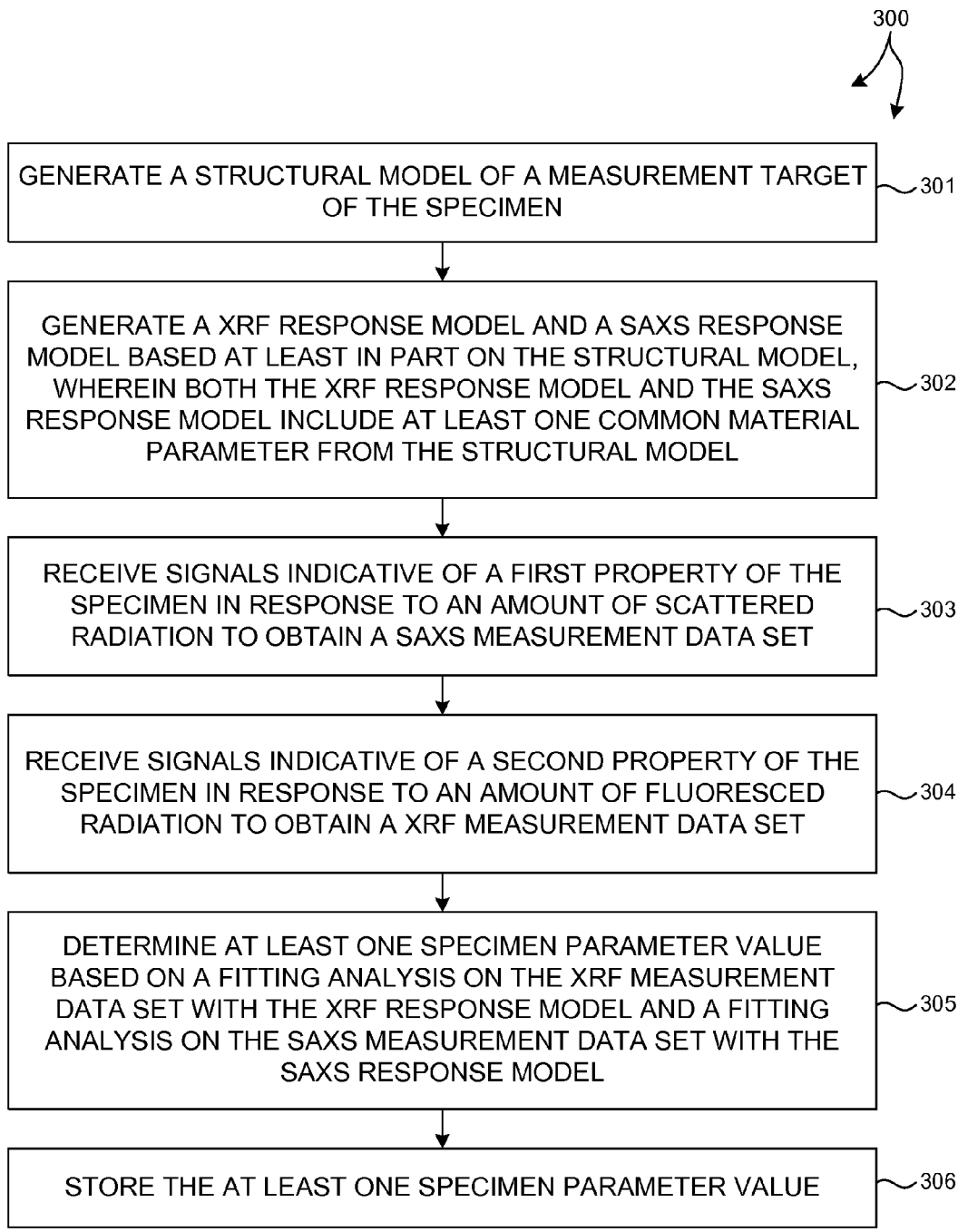
FIG. 6 is a flowchart illustrative of an exemplary method 300 of determining specimen parameter values based on a fitting analysis that includes SAXS response models and XRF response models that share at least one common material parameter.

FIG. 6 illustrates a method 300 suitable for implementation by the combined metrology systems 100 and 400 of the present invention. In one aspect, it is recognized that data processing blocks of method 300 may be carried out via a pre-programmed algorithm executed by one or more processors of computing system 130. While the following description is presented in the context of combined metrology systems 100 and 400, it is recognized herein that the particular structural aspects of combined metrology systems 100 and 400 do not represent limitations and should be interpreted as illustrative only.

In block 301, a structural model of a measurement target of a specimen is generated.

In block 302, a XRF response model and a SAXS response model are generated based at least in part on the structural model. Both the XRF response model and the SAXS response model include at least one common material parameter from the structural model.

In block 303, signals indicative of a first property of the specimen are received. The signals are generated in response to an amount of scattered radiation detected from the specimen in response x-ray illumination. The signals comprise a SAXS measurement data set.

In block 304, signals indicative of a second property of the specimen are received. The signals are generated in response to an amount of fluoresced radiation detected from the specimen in response x-ray illumination. The signals comprise a XRF measurement data set.

In block 305, at least one specimen parameter value is determined based on a fitting analysis on the XRF measurement data set with the XRF response model and a fitting analysis on the SAXS measurement data set with the SAXS response model.

In block 306, the specimen parameter value is stored in a memory (e.g., memory 132).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology tool comprising:
   at least one x-ray illumination source configured to generate an amount of incident x-ray radiation directed to a specimen;
   a first x-ray detector configured to receive an amount of radiation scattered from the specimen in response to the incident x-ray radiation and generate signals indicative of a first property of the specimen, wherein the at least one x-ray illumination source and the first x-ray detector are disposed in a Small Angle X-Ray Scatterometry (SAXS) measurement configuration; and
   a second x-ray detector configured to receive an amount of radiation fluoresced from the specimen in response to the incident x-ray radiation and generate signals indicative of a second property of the specimen, wherein the at least one x-ray illumination source and the second x-ray detector are disposed in a X-Ray Fluorescence (XRF) measurement configuration.

2. The metrology tool of claim 1, further comprising:
   an x-ray illumination optics subsystem configured to shape and direct the incident x-ray radiation to the specimen over a first inspection area of the specimen.

3. The metrology tool of claim 1, further comprising:
   a first x-ray illumination optics subsystem configured to shape and direct a first portion of the incident x-ray radiation to the specimen over a first inspection area of the specimen, wherein the first portion of the incident x-ray radiation is generated by a first x-ray illumination source; and
   a second x-ray illumination optics subsystem configured to shape and direct a second portion of the incident x-ray radiation to the specimen over a second inspection area of the specimen, wherein the second portion of the incident x-ray radiation is generated by a second x-ray illumination source.

4. The metrology tool of claim 2, further comprising:
   a beam controller operable to communicate a command signal to the x-ray illumination optics subsystem to redirect the incident x-ray radiation, wherein the command signal is determined based at least in part on the amount of radiation received by the first x-ray detector.

5. The metrology tool of claim 1, further comprising:
a wafer positioning system configured to selectively position the specimen at a plurality of different orientations out of plane from a planar surface of the specimen, wherein the wafer positioning system is configured to selectively position the specimen within a range of at least one degree about one or more axes of rotation aligned in-plane with the surface of the specimen.

6. The metrology tool of claim 1, further comprising:
a model building and analysis engine configured to:
generate a structural model of a measurement target of the specimen;
generate a XRF response model and a SAXS response model based at least in part on the structural model, wherein both the XRF response model and the SAXS response model include at least one common material parameter from the structural model;
receive the signals generated by the first x-ray detector to obtain a SAXS measurement data set;
receive the signals generated by the second x-ray detector to obtain a XRF measurement data set;
determine at least one specimen parameter value based on a fitting analysis on the XRF measurement data set with the XRF response model and a fitting analysis of the SAXS measurement data set with the SAXS response model; and
store the at least one specimen parameter value.

7. The metrology tool of claim 6, wherein a value of the at least one common material parameter is determined based on the fitting analysis on the XRF measurement data set and the determined value is treated as a constant in the fitting analysis of the SAXS measurement data set.

8. The metrology tool of claim 6, wherein the at least one common material parameter is treated as a global parameter in a parallel fitting analysis including both the fitting analysis on the XRF data set and the fitting analysis of the SAXS data set.

9. The metrology tool of claim 1, wherein the at least one x-ray illumination source and the first x-ray detector are disposed in a Transmission Small Angle X-Ray Scatterometry (T-SAXS) or a grazing incidence Small Angle X-ray Scatterometry (GI-SAXS) configuration.

10. The metrology tool of claim 1, wherein the at least one x-ray illumination source and the second x-ray detector are disposed in a confocal XRF measurement configuration or a total reflection XRF configuration.

11. The metrology tool of claim 1, wherein the at least one x-ray illumination source comprises,
an electron beam source configured to direct an electron beam at a primary target that generates an amount of primary radiation in response to the electron beam, and
a secondary target that receives the amount of primary radiation and generates the amount of incident x-ray radiation in response to the amount of primary radiation.

12. A method comprising:
illuminating a specimen with an amount of incident x-ray radiation generated by at least one x-ray illumination source;
receiving an amount of radiation scattered from the specimen in response to the incident x-ray radiation on a first x-ray detector, wherein the at least one x-ray illumination source and the first x-ray detector are disposed in a Small Angle X-Ray Scatterometry (SAXS) measurement configuration;
generating signals indicative of a first property of the specimen in response to the amount of scattered radiation;
receiving an amount of radiation fluoresced from the specimen in response to the incident x-ray radiation on a second detector, wherein the at least one x-ray illumination source and the second x-ray detector are disposed in a X-Ray Fluorescence (XRF) measurement configuration;
generating signals indicative of a second property of the specimen in response to the amount of fluoresced radiation; and
storing an indication of the signals indicative of the first and second properties of the specimen.

13. The method of claim 12, further comprising:
redirecting at least a portion of the amount of incident x-ray radiation based on the received amount of radiation scattered from the specimen.

14. The method of claim 12, further comprising:
rotating the specimen to a plurality of different orientations out of plane from the surface of the specimen.

15. The method of claim 12, further comprising:
generating a structural model of a measurement target of the specimen;
generating a XRF response model and a SAXS response model based at least in part on the structural model, wherein both the XRF response model and the SAXS response model include at least one common material parameter from the structural model;
receiving the signals indicative of a first property of the specimen in response to the amount of scattered radiation to obtain a SAXS measurement data set;
receiving the signals indicative of a second property of the specimen in response to the amount of fluoresced radiation to obtain a XRF measurement data set;
determining at least one specimen parameter value based on a fitting analysis on the XRF measurement data set with the XRF response model and a fitting analysis of the SAXS measurement data set with the SAXS response model; and
storing the at least one specimen parameter value.

16. The method of claim 15, further comprising:
determining a value of the at least one common material parameter based on the fitting analysis on the XRF measurement data set, wherein the determined value is treated as a constant in the fitting analysis of the SAXS measurement data set.

17. The method of claim 15, further comprising:
determining a value of the at least one common material parameter based on a parallel fitting analysis including both the fitting analysis of the XRF data set and the fitting analysis of the SAXS data set.

18. A metrology system comprising:
at least one x-ray illumination source configured to generate an amount of incident x-ray radiation directed to a specimen;
a first x-ray detector configured to receive an amount of radiation fluoresced from the specimen in response to the incident x-ray radiation and generate a first signal indicative of the amount of x-ray radiation detected by the first x-ray detector, wherein the at least one x-ray illumination source and the first x-ray detector are disposed in a XRay Fluorescence (XRF) measurement configuration;
a second x-ray detector configured to receive an amount of radiation scattered from the specimen in response to the incident x-ray radiation and generate a second signal indicative of the amount of x-ray radiation detected by the second x-ray detector, wherein the at least one x-ray illumination source and the second x-ray detector are disposed in a Small Angle X-Ray Scatterometry (SAXS) measurement configuration; and a non-transitory, computer-readable medium, comprising:

code for causing a computer to generate a structural model of a measurement target of the specimen illuminated by the amount of x-ray radiation;

code for causing the computer to generate a XRF response model and a SAXS response model based at least in part on the structural model, wherein both the XRF response model and the SAXS response model include at least one common material parameter from the structural model;

code for causing the computer to determine at least one specimen parameter value based on a fitting analysis of the first signal with the XRF response model and a fitting analysis on the second signal with the SAXS response model; and code for causing the computer to store the at least one specimen parameter value.

19. The metrology system of claim 18, the non-transitory, computer-readable medium, further comprising:

code for causing the computer to determine a value of the at least one common material parameter based on the fitting analysis on the first signal, wherein the determined value of the at least one common material parameter is treated as a constant in the fitting analysis on the second signal.

20. The metrology system of claim 18, the non-transitory, computer-readable medium, further comprising:

code for causing the computer to determine a value of the at least one common material parameter based on a parallel fitting analysis on the first signal with the XRF response model and on the second signal with the SAXS response model.

* * * * *